United States Patent
Zhao et al.

(10) Patent No.: US 12,279,759 B2
(45) Date of Patent: Apr. 22, 2025

(54) DENTAL IMAGING DEVICE

(71) Applicant: Hangzhou Iscanbot Co., Ltd., Hangzhou (CN)

(72) Inventors: Zeyu Zhao, Hangzhou (CN); Jianqiao Cui, Hangzhou (CN)

(73) Assignee: HANGZHOU ISCANBOT CO., LTD., Hangzhou (CN)

( * ) Notice: Subject to any disclaimer, the term of this patent is extended or adjusted under 35 U.S.C. 154(b) by 155 days.

(21) Appl. No.: 18/117,473

(22) Filed: Mar. 5, 2023

(65) Prior Publication Data
US 2023/0293001 A1  Sep. 21, 2023

(30) Foreign Application Priority Data
Mar. 21, 2022  (CN) .......................... 202220617972.5

(51) Int. Cl.
*A61B 1/24* (2006.01)

(52) U.S. Cl.
CPC ..................................... *A61B 1/24* (2013.01)

(58) Field of Classification Search
CPC .................................. A61B 1/24; A61B 5/682
See application file for complete search history.

(56) References Cited

U.S. PATENT DOCUMENTS

| | | | |
|---|---|---|---|
| 2018/0303579 | A1 | 10/2018 | Salah et al. |
| 2021/0282634 | A1* | 9/2021 | Oren-Artzi ............ A61B 1/042 |
| 2022/0338723 | A1* | 10/2022 | Farkash ................. A61B 1/053 |
| 2022/0338727 | A1* | 10/2022 | Chambers ............ A61B 1/0014 |
| 2023/0301502 | A1* | 9/2023 | Rayman .................... A61B 1/07 |
| 2024/0122689 | A1* | 4/2024 | Pellissard ............ H04B 1/3877 |
| 2024/0126153 | A1* | 4/2024 | Pellissard ............ G03B 17/565 |
| 2024/0164631 | A1* | 5/2024 | Eilat-Bloch .......... A61B 1/0014 |

* cited by examiner

*Primary Examiner* — Julianna N Harvey
(74) *Attorney, Agent, or Firm* — Birch, Stewart, Kolasch & Birch, LLP

(57) ABSTRACT

In one aspect, the present application provides a dental imaging device, it comprises: a base, an elongated light blocking housing, a retractor and an attachment mechanism, wherein the elongated light blocking housing is mounted on a first side of the base and defines a channel, the retractor is for opening a user's lips and is provided on a first end away from the base of the elongated light blocking housing, the attachment mechanism is mounted on a second side opposite to the first side of the base for securing an image capturing device so that the image capturing device is able to capture images of the user's teeth, which are exposed by opening the user's lips with the retractor, through the channel, the elongated light blocking housing is mounted on a rectilinear rail on the base and its position along the rectilinear rail is adjustable.

10 Claims, 4 Drawing Sheets

DENTAL IMAGING DEVICE

FIELD OF THE APPLICATION

The present application generally relates to a dental imaging device.

BACKGROUND

After orthodontic treatment, because of certain reasons, a patient might have orthodontic relapse. In order to discover and correct such relapse, a dental professional needs to examine the patient's teeth regularly.

A device for capturing images of a patient's teeth which can be operated by the patient emerged to reduce times that the patient visits a clinic for dental examination. With such device, the patient can capture images of his/her own teeth anywhere anytime, and provide the captured images to a dental professional for examination, to reduce times that the patient visits a clinic for dental examination.

Reference is made to the US patent publication number US2018/0303579A1, which discloses a dental imaging device comprising a light blocking housing. One end of the light blocking housing is provided with a retractor for retracting lips/cheek of a patient to have the patient's teeth exposed, and the other end of the light blocking housing is provided with means for fixing a smart mobile phone for capturing images of the exposed teeth. However, the dental imaging device is clumsy in structure, and it is inconvenient to adjust the relative position between the image capturing device and the light blocking housing to align them to capture proper images of the patient's teeth.

Therefore, it is necessary to provide a new dental imaging device.

SUMMARY

In one aspect, the present application provides a dental imaging device, it comprises: a base, an elongated light blocking housing, a retractor and an attachment mechanism, wherein the elongated light blocking housing is mounted on a first side of the base and defines a channel, the retractor is for opening a user's lips and is provided on a first end away from the base of the elongated light blocking housing, the attachment mechanism is mounted on a second side opposite to the first side of the base for securing an image capturing device so that the image capturing device is able to capture images of the user's teeth, which are exposed by opening the user's lips with the retractor, through the channel, the elongated light blocking housing is mounted on a rectilinear rail on the base and its position along the rectilinear rail is adjustable.

In some embodiments, the rectilinear rail extends along a first direction, the position of the image capturing device on the attachment mechanism is adjustable along a second direction different from the first direction.

In some embodiments, the first and the second directions are perpendicular to each other.

In some embodiments, the first direction is the up and down direction of the user's mouth, and the second direction is the left and right direction of the user's mouth.

In some embodiments, the attachment mechanism comprises a pair of gripping jaws which grip the image capturing device along the first direction.

In some embodiments, at least one of the two opposite sides of a second end opposite to the first end of the light blocking housing is mounted on the rectilinear rail.

In some embodiments, the two opposite side of the second of the light blocking housing are distributed along a second direction perpendicular to a first direction along which the rectilinear rail extends.

In some embodiments, a rack and a retention means are provided on the light blocking housing and the base, respectively; when the rack and the retention means are engaged, the light blocking housing and the base are fixed relative to each other, when the rack and the retention means are disengaged, the light blocking housing is able to move along the rectilinear rail relative to the base.

In some embodiments, the rack is mounted on a second end opposite to the first end of the light blocking housing, and the retention means is mounted on the base.

In some embodiments, the rectilinear rail is a sliding groove, and the light blocking housing and the rack are respectively located on two opposite sides of the sliding groove.

In some embodiments, the retention means comprises a leaf spring, a section of which forms a V-shape to engage the rack.

In some embodiments, an opening through the first and the second sides is formed on the base, and the size of the opening along a first direction, along which the rectilinear rail extends, is greater than the size of the light blocking housing along the first direction.

BRIEF DESCRIPTION OF THE DRAWINGS

The above and other features of the present application will be further illustrated below with reference to figures and their detailed description. It should be appreciated that these figures only show several exemplary embodiments according to the present application, so they should not be construed as limiting the protection scope of the present application. Unless otherwise specified, the figures are not necessarily drawn to scale, and similar reference numbers therein denote similar components.

DETAILED DESCRIPTION OF ILLUSTRATED EMBODIMENTS

In the following detailed description, reference is made to the accompanying drawings, which form a part thereof. Exemplary embodiments in the detailed description and figures are only intended for illustration purpose and not meant to be limiting. Inspired by the present application, those skilled in the art can understand that other embodiments may be utilized and other changes may be made, without departing from the spirit or scope of the present application. It will be readily understood that aspects of the present application described and illustrated herein can be arranged, replaced, combined, separated and designed in a wide variety of different configurations, all of which are explicitly contemplated and make part of the present application.

One aspect of the present application provides a dental imaging device. Relative position between a light blocking housing and a base of the dental imaging device may be adjusted along a rectilinear rail. When a rack and a retention means provided on the light blocking tube and the base respectively are engaged, the relative position between the light blocking housing and the base is fixed. When the track and the retention means are disengaged, the light blocking housing and the base can slide relative to each other along the rectilinear rail, so that itis very convenient to adjust the relative position between an image capturing device secured on the base and the light blocking housing to have them aligned.

Figure 1:
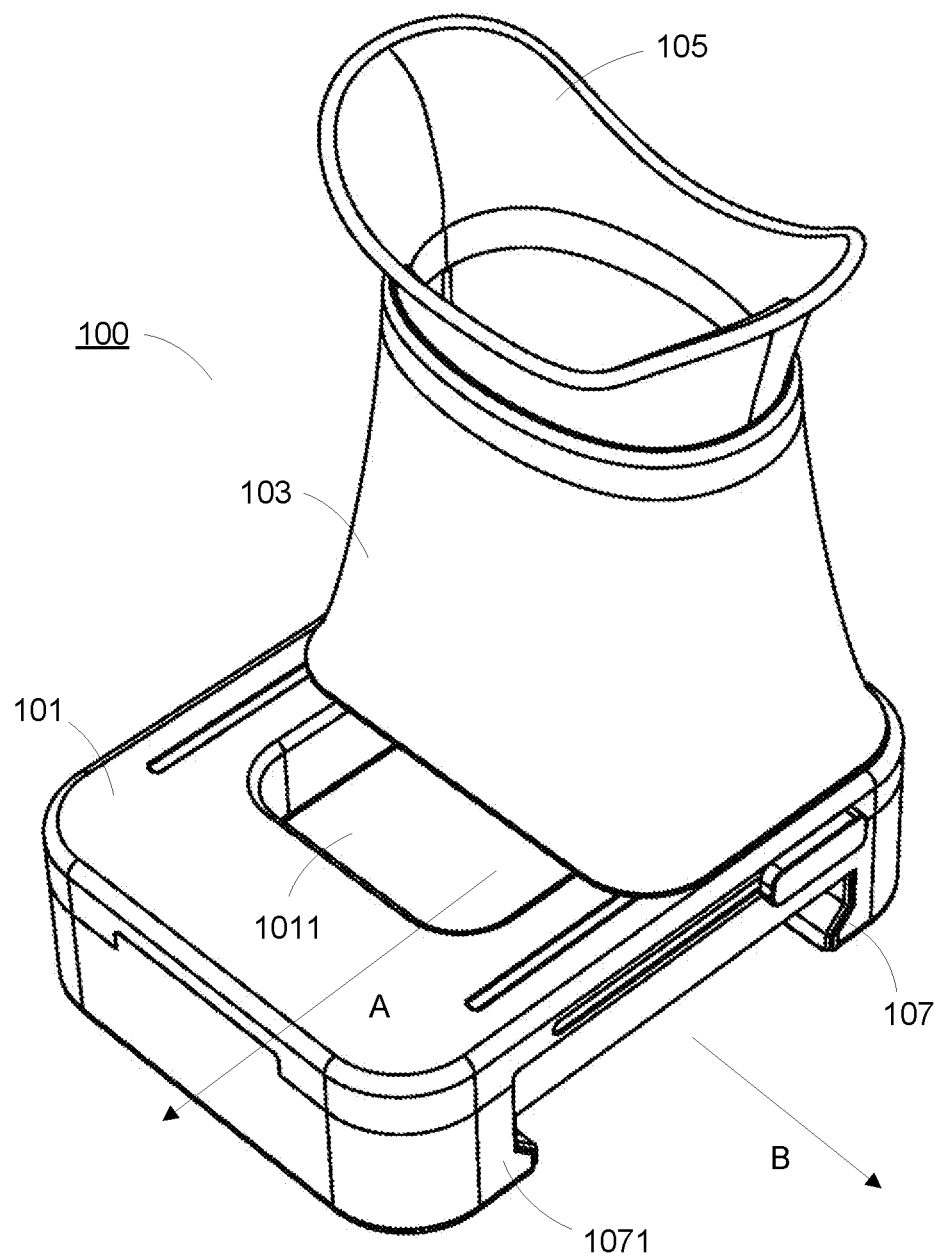
FIG. 1 schematically illustrates a dental imaging device according to one embodiment of the present application.

Referring to FIG. 1, it schematically illustrates a dental imaging device 100 according to one embodiment of the present application.

The dental imaging device 100 comprises a base 101, a light blocking housing 103, a retractor 105 and an attachment mechanism 107.

The base 101 forms an opening 1011 through its two opposite sides, namely a first side and a second side.

The light blocking housing 103 is an elongated pipe and defines a channel. The sizes and shapes of two opposite ends of the light blocking housing may be different or same. The light blocking housing is mounted on the first side of the base 101, and its position on the base is adjustable along a first axis A, such that the center of the light blocking housing 103 can be moved onto a line perpendicular to the first axis A, on which line the center of an image capturing device (not shown) lies, which image capturing device is secured on the second side of the base 101 opposite to the first side by the attachment mechanism 107.

On the one hand, the light blocking housing 103 at least partially blocks the external environment to reduce "noises" in the captured pictures and to reduce effect of ambient light on the captured images. On the other hand, it provides support for the retractor 105.

Figure 2:
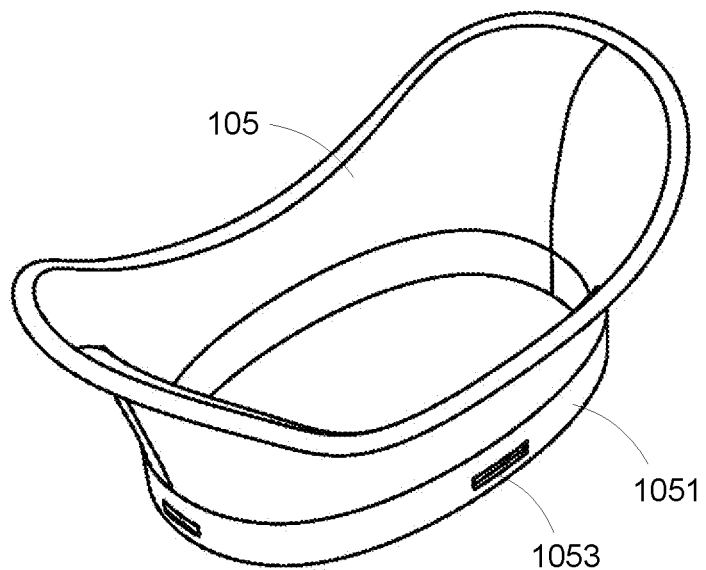
FIG. 2 schematically illustrates the retractor shown in FIG. 1.

Referring to FIG. 2, it schematically illustrates the retractor 105 of the dental imaging device 100 shown in FIG. 1.

Two opposite sides of one end of the retractor 105 away from the light blocking housing 103, corresponding to the left and right sides of an oral cavity, extend outward and form a horn shape for opening a user's lips, such that images of the user's teeth can be captured. The other end of the retractor 105 closer to the light blocking housing 103 forms a connecting part 1051 whose shape and size match one end of the light blocking housing 103 away from the base 101. The retractor 105 is mounted on the light blocking housing 103 by inserting the connecting part 1051 into the light blocking housing 103. At least one snap-fitting opening 1053 is formed on the connecting part 1051 which engages a protruding structure (not shown) formed at a corresponding position on the inner wall of the light blocking housing 103, to fix the retractor 105 to the light blocking housing 103.

It is understood that in addition to the retention structure in the above embodiment, any other suitable retention structure may be used to fix the retractor 105 on the light blocking housing 103. For example, a protruding structure may be formed on the connecting part 1051, and a recessed structure for engaging the protruding structure may be formed on the inner wall of the light blocking housing 103. In another example, the outside of the connecting part 1051 may be provided with a layer of soft elastic material (e.g., silicone) whose size is slightly larger than the inner size of the light blocking housing 103. When the connecting part 1051 is inserted into the light blocking housing 103, interference fit between the two is achieved, and the retractor 105 is fixed on the light blocking tube 103.

The size of a cross section of the connecting part 1051 along a transverse direction (a direction corresponding to a left-right direction of a user's mouth) is greater than its size along a height direction (a direction corresponding to an up-down direction of the user's mouth), and the two opposite sides of the edge contour line of the cross section of the connecting part 1051 along the transverse direction are smooth arc lines.

In the above embodiment, the light blocking housing 103 is sleeved on the connecting part 1051. It is understood that in another embodiment, the connecting part 1051 may be sleeved on the light blocking housing 103.

After each use, the user's saliva might remain on the retractor 105. For purpose of hygiene, after and before each use, the retractor 105 may be cleaned, and the detachable retractor 105 makes the cleaning very convenient.

Figure 3:
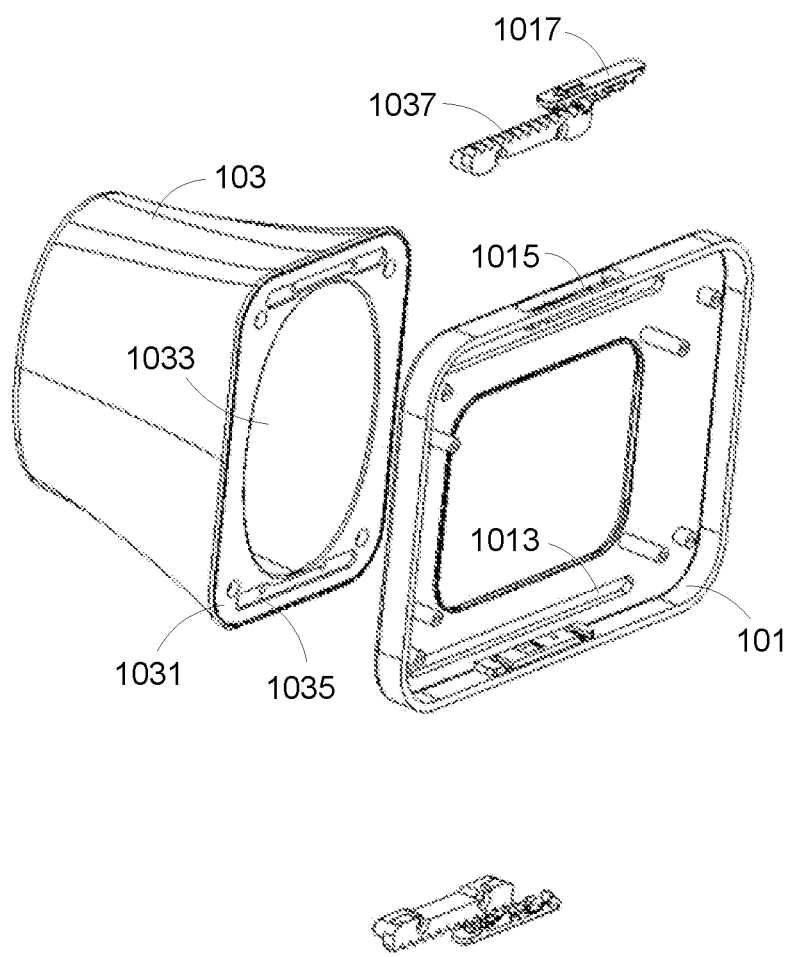
FIG. 3 schematically illustrates how the light blocking housing and the base shown in FIG. 1 are assembled.

Referring to FIG. 3, it schematically illustrates how the base 101 and the light blocking housing 103 are assembled.

A bottom plate 1031 is provided on one end closer to the base 101 of the light blocking housing 103, and an opening 1033 is formed in the middle of the bottom plate 1031 so that the image capturing device is able to capture pictures of the user's teeth through the light blocking housing 103. A rack mounting part 1035 is formed on each of two opposite sides of the bottom plate 1031 along the transverse direction of the oral cavity for mounting a rack 1037. In another embodiment, the bottom plate 1031 and the light blocking housing 103 may be formed integrally. In a further embodiment, the bottom plate 1031 may be fixed to the light blocking housing 103, for example using screws.

A sliding groove 1015 is formed on each of two opposite sides of the base 101 corresponding to the rack mounting parts 1035. The transverse size of the rack 1037 is greater than that of the sliding groove 1015 such that the racks 1037 and the light blocking housing 103 are respectively on two opposite sides of sliding groove 1015, and the relative degree of freedom along the extending direction of the light blocking housing 103 between the light blocking housing 103 and the base 101 is limited. The light blocking housing 103 and the base 101 can slide relative to each other along the sliding grooves 1013.

The teeth of the racks 1037 face towards the outside of the base 101. An opening 1015 is formed at a corresponding position of the sidewall of the base 101 to mount the retention means 1017. The retention means 1017 and the rack 1037 together control whether the light blocking housing 103 and the base 101 are fixed or slidable relative to each other.

Figure 4:
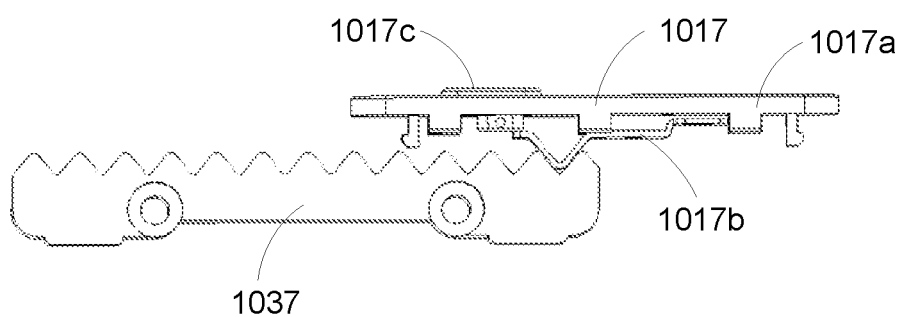
FIG. 4 schematically illustrates how the rack and the retention means shown in FIG. 3 are engaged.

Referring to FIG. 4, it schematically illustrates how the retention means 1017 and the rack 1037 are engaged.

The retention means 1017 comprises a base plate 1017a, a leaf spring 1017b and a slider (button) 1017c. A first end of the leaf spring 1017b is fixed on the base plate 1017a, and a V-shape is formed adjacent to a second end opposite to the first end with the tip of the V-shape facing the rack 1037. The slider 1017c can slide relative to the base plate 1017a along the extending direction of the leaf spring 1017b, and is fixed relative to the second end of the leaf spring 1017b.

When the V-shape of the leaf spring 1017b engages the rack 1037, the light blocking housing 103 and the base 101 remain fixed relative to each other. If the relative position between the light blocking housing 103 and the base 101 need to be adjusted, a force is applied to move the slider 1017c in a direction away from the first end of the leaf spring 1017b, thereby making the V-shape of the leaf spring 1017b to deform so that the V-shape and the rack 1037 are disengaged, and the light blocking housing 103 is able to move along the sliding groove 1015. After the light blocking housing 103 is moved to a desired position, the slider 1017c is released, and the leaf spring 1017b elastically restores the V-shape and re-engages the rack 1037 so that the light blocking housing 103 and the base 101 are fixed with each other again and the light blocking housing 103 is kept at the desired position.

In another embodiment, the slider 1017c may slide relative to the leaf spring 1017b. When the slider 1017c abuts against the second end of the leaf spring 1017b, it urges the V-shape to engage the rack 1037, an external force is not prone to make the V-shape slide out of two adjacent teeth of the rack 1037, and the light blocking housing 103 and the base 101 are fixed with each other. When the slider 1017c slides to the first end of the leaf spring 1017b, the second end of the leaf spring 1017b loses support from the slider 1017c and become a cantilever. At this time, a small force applied to the light blocking housing 103 can cause the V-shape of the leaf spring 1017c to slide out of two adjacent teeth of the rack 1037, and the relative position between the light blocking housing 103 and the base 101 can be adjusted. After the light blocking housing 103 is moved to a desired position, the slider 1017c is moved back to the second end of the leaf spring 1017b so that the light blocking housing 103 and the base 101 are fixed with each other again.

Inspired by the present application, it is understood that modifications may be made to the above embodiments. For example, the base 101 may be provided with a raised slide rail, and the light blocking housing 103 may be provided with a sliding groove for engaging the slide rail. In another example, the rack may be provided on the base 101, and the retention means for engaging the rack may be provided on the light blocking housing 103. In another example, in addition to the leaf spring formed with the V-shape, other elements may be used to engage the rack, for example a key that is able to be inserted between two adjacent teeth of the rack.

Referring to FIG. 1 again, an attachment mechanism 107 is mounted on the second side of the base 101 for securing the image capturing device on the base 101.

In the present embodiment, the attachment mechanism 107 comprises a pair of gripping jaws for gripping and securing the image capturing device. The position of the image capturing device can be adjusted along a B-axis perpendicular to the gripping direction of the gripping jaws 1071. The A-axis is perpendicular to the B-axis. Therefore, the image capturing device can be aligned with the center of the light blocking housing 103, namely, the center of the retractor 105, by adjusting the position of the light blocking housing 103 along the A-axis and the position of the image capturing device along the B-axis. When aligned, the image capturing device may be used to capture images of teeth exposed by opening lips of a user through the opening 1011, the light blocking housing 103 and the retractor 105.

It is understood that in addition to the gripping jaws, the attachment mechanism 107 may be any other suitable attachment mechanism.

The image capturing device may be any device capable of capturing pictures, for example, a smart mobile phone, a tablet computer etc.

While various aspects and embodiments have been disclosed herein, other aspects and embodiments will be apparent to those skilled in the art, inspired by the present application. The various aspects and embodiments disclosed herein are for illustration only and are not intended to be limiting, and the scope and spirit of the present application shall be defined by the following claims.

Likewise, the various diagrams may depict exemplary architectures or other configurations of the disclosed methods and systems, which are helpful for understanding the features and functions that can be included in the disclosed methods and systems. The claimed invention is not restricted to the illustrated exemplary architectures or configurations, and desired features can be achieved using a variety of alternative architectures and configurations. Additionally, with regard to flow diagrams, functional descriptions and method claims, the order in which the blocks are presented herein shall not mandate that various embodiments of the functions shall be implemented in the same order unless otherwise the context specifies.

Unless otherwise specifically specified, terms and phrases used herein are generally intended as "open" terms instead of limiting. In some embodiments, use of phrases such as "one or more", "at least" and "but not limited to" should not be construed to imply that the parts of the present application that do not use similar phrases intend to be limiting.

We claim:

1. A dental imaging device, comprising:
a base,
an elongated light blocking housing,
a retractor and
an attachment mechanism,
wherein the elongated light blocking housing is mounted on a first side of the base and defines a channel, the retractor is for opening a user's lips and is provided on a first end away from a base of the elongated light blocking housing, the attachment mechanism is mounted on a second side opposite to the first side of the base for securing an image capturing device so that the image capturing device is able to capture images of the user's teeth, which are exposed by opening the user's lips by the retractor, through the channel, the elongated light blocking housing is mounted to a rectilinear groove formed in a top surface of base on the first side of the base and the elongated light blocking housing is operable to move along the rectilinear groove in a first direction, and
wherein the base includes a first side surface and a second side surface that are perpendicular to said top surface, each of the first side surface and the second side surface includes an opening formed therethrough, the opening extends in the first direction, overlaps with the light blocking housing in a second direction perpendicular to the first direction, and has a length in the first direction greater than a maximum length of the light blocking housing along the first direction.

2. The dental imaging device according to claim 1, wherein the rectilinear groove extends along the first direction, the position of the image capturing device on the attachment mechanism is adjustable along the second direction.

3. The dental imaging device according to claim 2, wherein the attachment mechanism comprises a pair of gripping jaws which grip the image capturing device along the first direction.

4. The dental imaging device according to claim 1, wherein, when in use, the first direction is an up and down direction of the user's mouth, and the second direction is a left and right direction of the user's mouth.

5. The dental imaging device according to claim 1, wherein at least one of two opposite sides of a second end opposite to the first end of the light blocking housing is mounted on the rectilinear groove.

6. The dental imaging device according to claim 5, wherein the two opposite sides of the second end of the light blocking housing are distributed along the second direction perpendicular to the first direction along which the rectilinear groove extends.

7. The dental imaging device according to claim 1, wherein a rack and a retention means are provided on the light blocking housing and the base, respectively, when the rack and the retention means are engaged, the light blocking housing and the base are fixed relative to each other, when the rack and the retention means are disengaged, the light blocking housing is able to move along the rectilinear groove relative to the base.

8. The dental imaging device according to claim 7, wherein the rack is mounted on a second end opposite to the first end of the light blocking housing, and the retention means is mounted on the base.

9. The dental imaging device according to claim 7, wherein the rectilinear groove is a sliding groove, and the light blocking housing and the rack are respectively located on two opposite sides of the sliding groove.

10. The dental imaging device according to claim 7, wherein the retention means comprises a leaf spring, a section of which forms a V-shape to engage the rack.

* * * * *